United States Patent [19]

Rosenberger

[11] 3,998,856
[45] Dec. 21, 1976

[54] PREPARATION OF EPOXIDES

[75] Inventor: Michael Rosenberger, Caldwell, N.J.

[73] Assignee: Hoffmann-La Roche Inc., Nutley, N.J.

[22] Filed: Apr. 10, 1975

[21] Appl. No.: 566,893

[52] U.S. Cl. .................................. 260/348 R
[51] Int. Cl.$^2$ ........................... C07D 301/02
[58] Field of Search ............................ 260/348 R

[56] References Cited

UNITED STATES PATENTS 3,442,912  5/1969  Hatch ........................... 260/348 R

OTHER PUBLICATIONS

A. Merz et al., Angew. Chem. Internat. Edit., vol. 12, (1973), No. 10, pp. 845–846.
Y. Yano et al., Jour. Chem. Soc. Chem. Comm. (1973), pp. 527–528.

Primary Examiner—Norma S. Milestone
Attorney, Agent, or Firm—Samuel L. Welt; Bernard S. Leon; William H. Epstein

[57] ABSTRACT

Preparation of 1-(2,6,6-trimethyl-1-cyclohexenyl)-3-methyl-3,4-epoxy-but-1-ene from β-ionone by utilizing trimethyl sulfonium chloride in the presence of a phase transfer catalyst and a base; or by utilizing a higher alkyl dimethyl sulfonium salt in the presence of a base.

4 Claims, No Drawings

PREPARATION OF EPOXIDES

BACKGROUND OF THE INVENTION

In the past, trialkyl sulfonium halides have been utilized as methylene transfer agents in conjunction with aldehydes. Hatch in Journal of Organic Chemistry 34 2133 (1969) disclosed that sulfonium halides in sodium hydroxide can be utilized to transfer alkyl and alkenyl groups to activated aldehydes particularly those aldehydes having an $\alpha, \beta$ -unsaturation. See also U.S. Pat. No. 3,426,046, Feb. 4, 1969. Merz also reported in Angew Chem. 83 No. 19, page 867 (1973), that phase transfer catalysts can be utilized in conjunction with alkylsulfonium iodides as methylene transfer agents for acetophenone giving yields of 36% in 72 hours. In order to increase the yields with methylene transfer agents, Yano et al. disclosed in J.C.S. Chem. Comm., 527 (1973) utilizing long chain alkyl dimethyl sulfonium salts such as lauryl dimethyl sulfonium halides as methylene transfer agents. It was through these long chain alkyl dimethyl sulfonium halides that good yields of the methylene addition product with ketones such as benzyl methyl ketone are obtained.

However, in the past, use of the trimethyl sulfonium halide salts as methylene transfer agents for ketones has not proven to be successful due to the low yields and long reaction times necessary to carry out this reaction. Therefore, the use of these cheap alkyl sulfonium halides as methylene transfer agents has been avoided for other than activated aldehydes.

SUMMARY OF THE INVENTION

In accordance with this invention, it has been discovered that a ketone, $\beta$-ionone which has the formula:

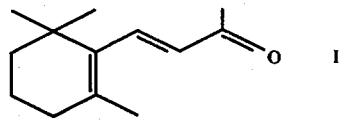

can be converted to an epoxide:

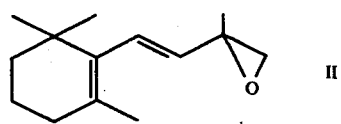

in high yields, i.e. yields of greater than 90% with a relatively short reaction times by treating $\beta$-ionone with a trimethyl sulfonium salt having the formula:

$$(CH_3)_3\ S^+\ X^- \qquad III$$

wherein X is a chloride, fluoride or hydroxide ion; in an alkali medium in the presence of a phase transfer catalyst.

The improved results as far as yields and reaction time are concerned is based upon the use of the particular trimethylsulfonium salt as the methylene transfer agent in combination with the phase transfer catalyst. If other sulfonium salts are utilized or if the phase transfer catalyst is not present, then the compound of formula II is not formed in the high yields with the relatively short reaction times. Furthermore, the reaction of this invention can be carried out with a methylene transfer agent utilizing relatively simple and economic solvents and reaction conditions.

The process of this invention involves a simple and efficient method for producing the epoxide of formula II without utilizing expensive solvents and handling techniques encountered by other procedures for reacting methylene transfer agents with oxo compounds.

In accordance with another embodiment of this invention, the compound of formula I can be converted to a compound of formula II utilizing a salt having the formula:

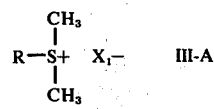

wherein R is higher alkyl and $X_1$ is chloride, fluoride, hydroxide or a $CH_3OSO_3$ ion;

in very high yields and in short reaction times.

DETAILED DESCRIPTION OF THE INVENTION

In accordance with this invention, $\beta$-ionone is converted to an epoxide of formula II in high yields of at least 90% by utilizing the trimethylsulfonium chloride, hydroxide, or fluoride salt of formula III as the methylene transfer agent in the presence of a phase transfer catalyst. In carrying out this reaction, any conventional phase transfer catalyst can be utilized. Among the preferred phase transfer catalysts are the quaternary ammonium salts. Any conventional quaternary ammonium salt can be utilized as the phase transfer catalyst in accordance with this invention. Among the preferred quaternary ammonium salts are compounds of the formula:

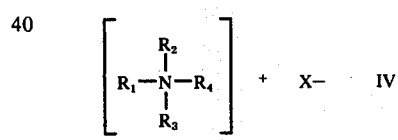

wherein $R_1$, $R_2$, $R_3$ and $R_4$ are alkyl or benzyl, and X is as above.

Particularly preferred among the phase transfer catalysts are:
N-tetramethyl ammonium chloride;
N-benzyl triethyl ammonium chloride;
N-tetraethyl ammonium chloride; and
N-n-hexadecyl trimethyl ammonium chloride.

The phase transfer catalyst is present in the reaction medium generally in catalytic quantities, i.e., from 100 mg. to 5 grams per mole of the ketone of formula I. While it is preferred that the phase transfer catalyst be present in catalytic quantities such as given above, this reaction can be carried out using greater than catalytic quantities of the phase transfer agent, i.e., over 1 mole of the phase transfer catalyst per mole of the ketone of formula I. However, since the use of large excesses of the phase transfer catalyst serves no beneficial purpose and substantially adds to the cost of the reaction, it is generally preferred to utilize a minimum amount of the phase transfer catalyst, i.e., no more than 5 grams of the phase transfer catalyst per mole of the ketone.

The reaction of this invention is carried out in a two phase system, i.e., an aqueous phase and an organic solvent phase. The aqueous phase contains a strong alkali metal or ammonium base. Among the strong bases which can be utilized are sodium hydroxide, and quaternary ammonium hydroxide. Any conventional quaternary ammonium hydroxide can be utilized such as the tetraalkyl ammonium hydroxides, i.e., tetraethyl ammonium hydroxides, as well as quaternary ammonium hydroxide salts of resins such as polystyrene. The base is present in the aqueous phase in an amount of from 12 molar to 20 molar. As the organic phase of this reaction medium, any conventional inert organic solvent can be utilized. Among the preferred inert organic solvents which can be utilized as the organic phase in this reaction are included hydrocarbon solvents such as pentane, hexane, toluene, benzene, etc.; halogenated hydrocarbon solvents such as methylene chloride, carbon tetrachloride, ethylene dichloride, etc.; ether solvents such as tetrahydrofuran, dioxane, diethyl ether, etc.; and thioethers such as dimethyl sulfide, diethyl sulfide, etc.

In carrying out this reaction, temperature and pressure are not critical and this reaction can be carried out at room temperature and atmospheric pressure. However, if desired, higher or lower temperatures can be utilized. Generally, it is preferred to carry out this reaction at a temperature of from 10° to 100° C. In accordance with this invention, it has been found that the reaction can take place at yields of greater than 90% in approximately 1 hour. If desired, longer reaction times can be utilized, i.e., up to 5 days, if desired. However, since no beneficial results are achieved by carrying out this reaction with such long reaction times, it is not necessary to utilize these long reaction times.

The $\alpha$, $\beta$ -unsaturated epoxide of formula I is converted to a compound having the formula:

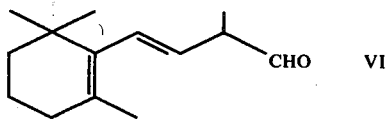 VI by treating the epoxide of formula I with a Lewis acid. Any conventional Lewis acid can be utilized in carrying out this reaction. Among the preferred Lewis acids are halides of metals such as magnesium, zinc, iron and aluminum. The partiularly preferred Lewis acid in the reaction is magnesium bromide. This reaction is carried out in an inert organic solvent preferably ether. In this reaction, any conventional inert organic solvent can be utilized, such as the di(lower alkyl) ethers, the aliphatic hydrocarbons, ethyl acetate or carbon tetrachloride. In this reaction, temperature and pressure are not critical, and any temperature of from about −90° c. and +50° C. and atmospheric pressure can be suitably utilized. Preferably, this reaction is carried out at a temperature of −10° C.

The $\beta$, $\delta$ -unsaturated aldehyde of formula VI can be isomerized to form the $\alpha,\beta$ -unsaturated aldehyde of the formula:

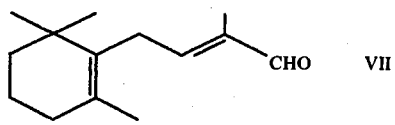 VII by treating the aldehyde of formula VI with an aqueous base. In this reaction, any conventional base can be utilized, such as the alkali metal and alkaline earth metal hydroxides, preferably the alkali metal hydroxides. This reaction can be suitably carried out in an inert or water-miscible, organic solvent such as a lower alkanol or a di(lower) alkyl ether or hydrocarbon (hexane, toluene) or thioether. Preferably, this reaction is carried out in the reaction medium in which the $\beta$, $\delta$ -unsaturated aldehyde of formula VI is formed. In this reaction, temperature and pressure are not critical, and the reaction can be suitably carried out at room temperature and atmospheric pressure. Generally, it is preferred to carry out this reaction at a temperature of from 0° to 70° C. It is also preferred to have a phase transfer catalyst present in the isomerization reaction.

The process of this invention is extremely advantageous since it produces in high yields the compound of formula VII utilizing a low cost methylene transfer agent, i.e., trimethyl sulfonium chloride, fluoride or hydroxide salts. The compound of formula VII is a known intermediate for vitamin A. Therefore, the process of this invention provides an effective and economical means for converting $\beta$-ionone to vitamin A.

In accordance with another embodiment of this invention, the compound of formula I can be converted to the compound of formula II utilizing the sulfonium salt of formula III-A. In this reaction, there is no need to utilize the phase transfer catalyst. In utilizing the sulfonium salt of formula III-A, the reaction is carried out in the same manner as described in connection with the use of a compound of the formula III in this reaction, except that there is no need to utilize the phase transfer catalyst of formula IV.

The term "alkyl" as used in this application comprehends lower alkyl groups containing from 1–7 carbon atoms such as methyl, ethyl, isopropyl, etc.; as well as higher alkyl groups containing from 8–18 carbon atoms such as n-hexadecyl, n-tetradecyl and n-dodecyl.

The Examples which follow further illustrate the invention. Unless otherwise stated, all temperatures are in degrees Centigrade (°C.).

EXAMPLE 1

A mixture of 24 grams of trimethylsulfonium chloride and 38.4 grams of $\beta$-ionone dissolved in 100 ml. of dichloromethane containing 1 gram of N-benzyltriethylammonium chloride and 125 ml. of an aqueous caustic soda solution (18 Molar) was stirred vigorously for 9½ hours at room temperature and then filtered free of solids. Removal of the organic solvents "in vacuo" yielded 41.5 grams of 1-(2,6,6-trimethyl-1-cyclohexenyl)-3-methyl-3,4-epoxy-but-1-ene.

EXAMPLE 2

1-(2,6,6-trimethyl-1-cyclohexenyl)-3-methyl-3,4-epoxy-but-1-ene was dissolved in 150 ml. of toluene and added rapidly to a slurry of 17 grams of magnesium bromide etherate in 150 ml. of toluene cooled to −40° C. The mixture was then stirred a further 10 minutes at −10° C. and quenched with 50 ml. of an aqueous ammonium chloride sodium (10% by weight) and stirred a further 5 minutes at ~ 15° C. The aqueous phase was removed and the toluene layer was then exposed to 3 g. of sodium hydroxide, dissolved in 60 ml. of aqueous methanol (1:2) and stirred for an additional 90 minutes at room temperature. The mixture was then filtered and the aqueous phase was washed with 50 ml. of toluene and the combined toluene extracts were then washed with 50 ml. of brine (saturated) and taken to dryness in vacuo. Distillation of the residue through a 4 inch vacuum jacketed vigreaux column yielded two fractions (i) b.p. 80°–90° C., 1 mm 1.8 g. of 1-(2,6,6-trimethyl-1-cyclohexenyl)3-methyl-2-buten-4-al assaying for 93% and (ii) b.p. 90°–94° C., 11 mm 35.2 g. of 1-(2,6,6-trimethyl-1-cyclohexenyl)-3-methyl-2-buten-4-al assaying for 98.5%. A pot residue of 2.6 g. was also obtained. This constitutes an overall yield of 90% yield of 100% pure 1-(2,6,6-trimethyl-1-cyclohexenyl)-3-methyl-2-buten-4-al from β-ionone.

EXAMPLE 3

150 mg. magnesium were treated with 0.54 ml. of dibromethane in 10 ml. of diethyl ether. The resulting two phase system containing magnesium bromide was cooled to −10° C. and treated with 5 g. 1-(2,6,6-trimethyl-1-cyclohexenyl)-3SR-methyl-3,4-epoxy-but-1-ene, dissolved in 10 ml. of diethyl ether. After 5 minutes at −10° C., the mixture was washed with water and dried over anhydrous sodium sulfate. Removal of the solvents in vacuo and distillation of the residue gave 3.9 g. 1-(2,6,6-trimethyl-1-cyclohexenyl)-3-methyl-1-buten-4-al; b.p. 77°–80° C./0.2 mm Hg.

EXAMPLE 4

6.18 g. of 1-(2,6,6-trimethyl-1-cyclohexenyl)-3-methyl-1-buten-4-al was dissolved in 15 ml. methanol and treated with 250 mg. KOH, dissolved in 0.3 ml. water and 5 ml. methanol, and left at room temperature for 35 minutes. Extraction with hexane and water, followed by distillation, gave 4.75 g. 1-(2,6,6-trimethyl-1-cyclohexenyl)-3-methyl-2-buten-4-al; b.p. 85°–88° C./0.5 mm Hg.

EXAMPLE 5

With Trimethyl Sulfonium Fluoride

A mixture of β-ionone (4 g.), toluene (10 ml.), benzyltriethylammonium chloride (0.1 g.) and squeous sodium hydroxide (10 ml.; 17.8 M) were treated with an aqueous solution of trimethyl sulfonium fluoride (2.7 g.; 70% solution) and stirred at room temperature for ½ hour. Dilution with hexane and water yielded 1-(2,6,6-trimethyl- 1-cyclohexenyl)-3-methyl-3,4-epoxy-but-1-ene (75% yield) on removal of the hexane solution. The product was identified by its characteristic nmr spectrum.

EXAMPLE 6

With Trimethyl Sulfonium Hydroxide

Silver nitrate (1 Mol) in water (40% by weight aqueous solution) was treated with sodium hydroxide (10 Mol. eq.) and the solid was filtered of and washer with methanol. The residue was then stirred at 0° C. with a solution of trimethylsulfonium chloride (0.75 Mol. eq.) in methanol (250 ml). The solids were filtered off and the solution was concentrated at room temperature and 0.5 mm Hg pressure to yield an aqueous solution of trimethyl sulfonium hydroxide (~60% by weight in H₂O). This aqueous solution (1 Mol. eq.) was stirred with β-ionone (40 g.) and 1 grams of benzyl triethyl ammonium chloride (100 ml.) at room temperature for 2 hours. Removal of the organic solvents in vacuo gave pure 1-(2,6,6-trimethyl-1-cyclohexenyl)-3-methyl-3,4-epoxy-but-1-ene.

EXAMPLE 7

1-(2,6,6-trimethyl-1-cyclohexenyl)-3-methyl-2-buten-4-al

Dodecyl dimethyl sulfonium chloride (66 g.; 89% purity) was combined with toluene (200 ml.) aqueous sodium hydroxide solution (100 ml.; 17 Molar) and treated at room temperature with β-ionone (38.4 g.) and stirred vigorously for 2½ hours. The solids were filtered off, washed with toluene and the toluene extracts were then separated completely from the aqueous layer. The final volume of toluene extract was 400 ml. and it contained 1-(2,6,6-trimethyl-1-cyclohexenyl)-3-methyl-3,4-epoxy-but-1-ene Magnesium bromide [anhydrous; prepared from Mg. (1.6 g.) and dibromoethane (4 ml.) in diethyl ether (50 ml.)] and cooled to −70° C. was treated rapidly with 400 ml. of the toluene solution containing 1-(2,6,6-trimethyl-1-cyclohexenyl)-3-methyl-3,4-epoxy-but-1-ene. The mixture was then stirred a further 10 minutes at −10° C. and quenched with a dilute ammonium chloride solution. The aqueous layer was removed and replaced with a dilute aqueous methanolic caustic soda solution (4 g. NaOH in 30 ml. H₂O and 60 ml. of methyl alcohol) and the two-phase mixture was stirred a further 1 hour at room temperature and then washed with brine. Removal of the solvents in vacuo gave the mixture of 1-(2,6,6-trimethyl-1-cyclohexenyl)-3-methyl-2-buten-4-al and dodecylmethyl sulfide which was added to hexane (100 ml.) and fed into a 1 inch by 10 foot Karr column at 2 ml/min. The other feed streams were hexane (11 ml/min) and acetonitrile (55 ml/min) which generated approximately 6 l. of acetonitrile extract and 1 l. of hexane. The acetonitrile fraction yielded the 1-(2,6,6-trimethyl-1-cyclohexenyl)-3-methyl-2-buten-4-al (34.6 g.) devoid of sulfide while the hexane extract gave the sulfide (53 g.) contaminated by 1-(2,6,6-trimethyl-1-cyclohexenyl)-3-methyl-2-buten-4-al (15%) (by glc analysis). This sulfide fraction was passed through a Karr column again as above to yield pure sulfide (44.2 g. > 98% pure by glc) and more 1-(2,6,6)-trimethyl-1-cyclohexenyl)-3-methyl-2-buten-4-al (8.4 g.) contaminated by the sulfide (ca 15%). The combined aldehyde fractions were distilled through a 10 cm. vacumn jacket vigreaux column to yield the 1(2,6,6-trimethyl-1-cyclohexenyl)-3-methyl-2-buten-4-al (35.4 g.) of 94% purity.

EXAMPLE 8

DODECYLDIMETHYLSULFONIUM METHOXYSULFATE

Dodecylmethyl sulfide (21.6 g.) was combined wigh dimethyl sulfate (12.6 g.) and heated at 100° C. for 2 hours. On cooling the mixture solidifed (34.3 g.), m.p. 75°–82° C. Crystallization from acetone yielded dodecyldimethylsulfonium methoxysulfate (32.5 g.) m.p. 75°–82° C.

EXAMPLE 9

A mixture of the dodecyldimethylsulfonium methoxysulfate (56.4 g.), β-ionone (28.8 g.), toluene (144 ml.) and aqueous caustic soda (17 Molar; 72 ml.) were stirred at room temperature for 2½ days and then filtered free of solids to yield a toluene layer comprised of a 1:1 molar ratio of 1-(2,6,6-trimethyl-1-cyclohexenyl)-3-methyl-3,4-epoxy-but-1-ene and dodecylmethyl sulfide.

I claim:

1. A process for producing an epoxide of the formula:

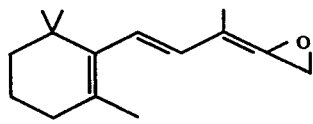

comprising reacting in a two phase system containing an inert organic solvent phase and an aqueous phase, a ketone of the formula:

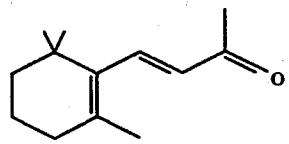

with trimethyl sulfonium fluoride or hydroxide in the presence of a phase transfer catalyst of the formula:

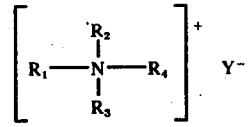

wherein $R_1$, $R_2$, $R_3$ and $R_4$ are benzyl or alkyl and Y is a chloride, fluoride or hydroxide; with said aqueous phase containing a base selected from the group consisting of an alkali metal or a quaternary ammonium hydroxide.

2. The process of claim 1 wherein said phase transfer catalyst is N-benzyltriethyl-ammonium chloride.

3. The process of claim 1 wherein said base is present in the aqueous medium in an amount to provide a concentration of from about 12 molar to about 20 molar aqueous solution of said base.

4. The process of claim 3 wherein said phase transfer catalyst is present in an amount of at least 100 mg. per mole of said ketone.

* * * * *